US006913598B2

(12) United States Patent
Tangri

(10) Patent No.: US 6,913,598 B2
(45) Date of Patent: Jul. 5, 2005

(54) HANDHELD EYE WASHING APPARATUS

(76) Inventor: Kuldip Chand Tangri, 8044 N. Harding Ave., Skokie, IL (US) 60076

(*) Notice: Subject to any disclaimer, the term of this patent is extended or adjusted under 35 U.S.C. 154(b) by 148 days.

(21) Appl. No.: 10/181,789

(22) PCT Filed: Jan. 22, 2001

(86) PCT No.: PCT/US01/01976

§ 371 (c)(1), (2), (4) Date: Oct. 9, 2002

(87) PCT Pub. No.: WO01/72261

PCT Pub. Date: Oct. 4, 2001

(65) Prior Publication Data

US 2003/0208168 A1 Nov. 6, 2003

Related U.S. Application Data

(63) Continuation-in-part of application No. 09/574,944, filed on May 19, 2000, now Pat. No. 6,458,108.

(60) Provisional application No. 60/177,584, filed on Jan. 22, 2000, and provisional application No. 60/176,657, filed on Jan. 18, 2000.

(51) Int. Cl.[7] .......................... A61M 35/00; A47K 1/00

(52) U.S. Cl. ............................ 604/297; 604/294; 4/625

(58) Field of Search ......................... 604/289, 294–302; 4/625; 128/200.23, 200.24; 222/527, 533, 556

(56) References Cited

U.S. PATENT DOCUMENTS

| | | | | | |
|---|---|---|---|---|---|
| 1,900,201 | A | * | 3/1933 | Sager | 604/296 |
| 2,524,720 | A | * | 10/1950 | Watrous | 604/296 |
| 2,524,972 | A | * | 10/1950 | Hamilton | 600/9 |
| 2,818,068 | A | * | 12/1957 | De Felice | 604/296 |
| 3,261,355 | A | * | 7/1966 | Burbig | 604/296 |
| 4,758,237 | A | * | 7/1988 | Sacks | 604/294 |
| 4,835,349 | A | * | 5/1989 | Weber | 200/38 R |
| 6,336,917 | B1 | * | 1/2002 | Berke | 604/295 |
| 6,398,766 | B1 | * | 6/2002 | Branch | 604/302 |
| 6,458,108 | B1 | * | 10/2002 | Tangri | 604/295 |
| 6,508,793 | B1 | * | 1/2003 | Harrold | 604/302 |
| 6,540,726 | B1 | * | 4/2003 | Follman et al. | 604/294 |

* cited by examiner

*Primary Examiner*—Kim M. Lewis

(57) ABSTRACT

This is a handheld eye flushing apparatus that comprises an eyecup that holds eyewash liquid in it for eye flushing. The rim of the eyecup is contoured to the eye orbit and rests on the eye orbital area. Attached to the inside of the eyecup is a stirring mechanism that stirs the eyewash liquid during usage. The force and duration of the stirring is predetermined to prevent eye damage. This apparatus accommodates the free movement of the eyelids and the eyeball inside the eyecup during utilization. The rim of this eyecup may have a liner to further increase comfort and liquid sealing around the eye. A magnetic strip may be placed near the bottom part of the rim to catch ferrous metal particles in industrial environment usage. A grid may be added between the rim and the agitator to keep the user away from the agitator.

33 Claims, 2 Drawing Sheets

HANDHELD EYE WASHING APPARATUS

This application is a 371 of PCT/US01/01976 filed Jan. 22, 2001, which claims benefit of 60/177,584 filed Jan. 22, 2000, and is a CIP of Ser. No. 09/574,944 filed May 19, 2000, now U.S. Pat. No. 6,458,108, which claims benefit of 60/176,657 filed Jan. 18, 2000 and claims benefit of 60/177,584 filed Jan. 22, 2000.

FIELD OF THE INVENTION

This invention relates to the maintenance and hygiene of the eye, specifically washing proteins, eyelash and foreign objects from the eye.

BACKGROUND OF THE INVENTION

Nature made eyes self-cleaning and lubricating. Sometimes due to unexplainable reasons or with aging it ceases to provide adequate tear flow which in turn causes the eye to feel crusty and tired. A satisfactory hygienic apparatus for eye washing is not readily available in the marketplace at the present time. There are numerous apparatuses existing, which can wash proteins from contact lenses for the eyes, but there is nothing currently available to wash the proteins from the actual eyes. The few eyecups, which do exist in the marketplace, are quite ineffective. U.S. Pat. No. 4,758,237 issued to Mr. Herman Sacks is relevant. In this patent Mr. Sacks tried to achieve an effective eye washer design but the design is inadequate. Starting with his eyecup, it does not cover enough of the area around the eye and it may be expensive to make. There are unfavorable possibilities of focusing the eyewash liquid towards the eye improperly and damage to the eyeball from the pressure buildup in chamber 3 if filter 8 is clogged. Further disadvantages, such as eyewash liquid contamination, high quantity of eyewash liquid utilization due to separate sump for the eyewash liquid and a pump, exist. Unlike Mr. Sacks's device, the present invention covers all of the eye and area around the eye. It is very inexpensive to make, it is adaptable due to its size, and there are no known flaws and no liquid lines from the pump. Also, there is no sump, sump pump, nor filter.

SUMMARY OF THE INVENTION

In this invention, an eyecup has a stirring mechanism to stir the eyewash liquid inside. The eye cup has an appropriate opening with an appropriate width rim contoured to fit the eye orbital and ample room for the eyelids and eyeball movement. Its rim is wider to accommodate the orbital variation and to get a better seal and comfort around the eye. Further, an optional soft-liner may be added to the rim. The stirring mechanism consists of an agitator and a driver for the agitator. The agitator is inside and the driver and its operating necessities are outside the eyecup. This device has a universal rim but because the contour of the left and the right eyes is different, it may be made contoured to the left and the right eye individually or jointly for both eyes. This is not shown in the diagrams because it is self-explanatory, and may be achieved with no problem. To make the present invention compact, components of the Handheld Eye Washing Apparatus may be laid out differently and an eyewash liquid warmer may be added to this apparatus.

The object of this invention is provide a handy, portable and inexpensive hygiene-aiding apparatus for the eye. It provides an effective flow of eyewash liquid to flush out the proteins and foreign objects from the eye and it is a boon for contact lens wearers.

DETAILED DESCRIPTION OF DRAWINGS

Figure 1:
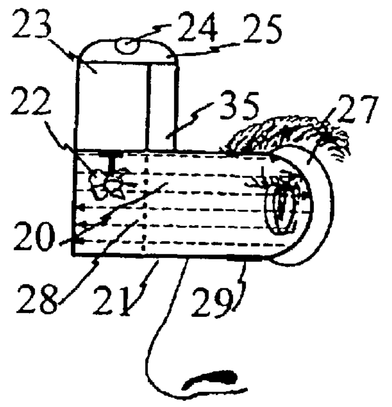
FIG. 1 is a side elevation view of the present invention, applied to the eye.

FIG. 1 is a side view of the apparatus that shows how it may be used. It is a one-piece molded throwaway type where a user uses it a certain number of times and throws it away like a toothbrush. In this figure, the user fills the eyecup 21 with eyewash liquid 20 and places it on the eye orbital area by tilting the head forward and bringing the head straight up. The momentary switch 24 is then pushed to activate the driver 23, which is an electrical motor where the driver is connected to the agitator 22 that turns inside of the eyecup 21, stirring or churning the eyewash liquid vigorously. Momentary switch 24 has an internal circuitry to stop the apparatus after a predetermined time. The driver 23 will stop even if the switch 24 is held on. To restart the driver 23 the momentary switch 24 must be released and pushed again. After the user is done with this procedure, he/she will take the eyecup 21 off by tilting his/her head forward, empty it to put it away after cleaning or refill it to repeat the process, if necessary. A housing 25 holds the driver 23, the power source and the momentary switch 24 for the driver 23. 35 is an access panel to the power source, such as a battery, for the driver 23 in the housing 25. Rim 27 of the eye cup 21 is contoured to fit the eye orbit. Grill 28 keeps the user away from the agitator 22. Magnetic strip 29 is molded into the eyecup 21 closer to the bottom part of the rim 27. If it is used as a first-aid apparatus in an industrial environment, during the utilization procedure, magnetic strip 29 will attract ferrous metal particles. Dotted lines and arrows 20 show eyewash liquid movement inside the eyecup 21.

Figure 2:
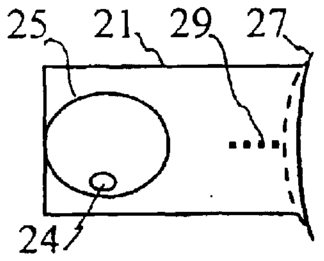
FIG. 2 is a top view of the apparatus.

FIG. 2 is the top view of the apparatus. It shows the eyecup 21, a momentary switch 24, housing 25 for the driver 23, the power source, and rim 27. Magnetic strip 29 is shown as the dotted line.

Figure 3:
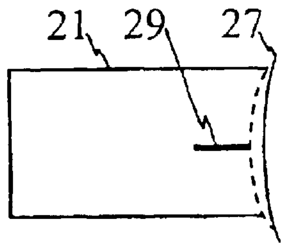
FIG. 3 is a bottom view of the apparatus.

FIG. 3 is a bottom view of the apparatus. It shows the eyecup 21, rim 27, and magnetic strip 29.

Figure 4:
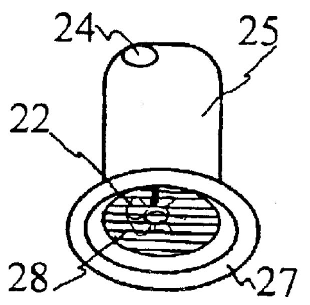
FIG. 4 is a frontal view or view from the rim of the apparatus.

FIG. 4 is a front view of the apparatus. It shows the rim 27 and through this rim 27, a grill 28; located further in is an agitator 22 and outside is the housing 25 to hold the driver 23 and required components for the driver 23. 24 is a momentary pushbutton switch.

Figure 5:
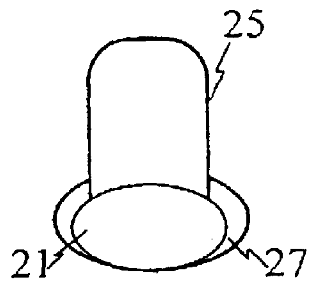
FIG. 5 is a rear view of the apparatus.

FIG. 5 is a rear view of the apparatus showing eyecup 21, rim 27 and housing 25 for the driver 23 and required components for the driver 23.

Figure 6:
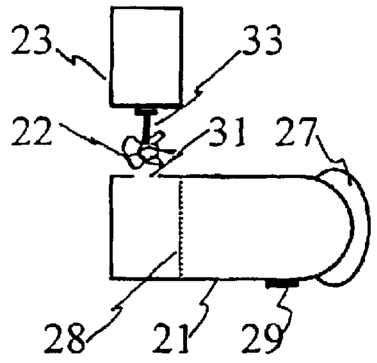
FIGS. 6, 7, and 8 illustrate disassembled apparatuses that show the assembly achievement of the agitator in different situations.

FIG. 6 shows the detached driver 23 from the eyecup 21 with the agitator 22 mounted on its shaft 33. In this embodiment, the shaft side of the driver 23 is watertight. When it is assembled, a portion of the driver 23 is press fitted into the opening 31 of the eyecup 21. Rim 27, grid 28, and magnetic strip 29 are shown in FIG. 6.

Figure 7:
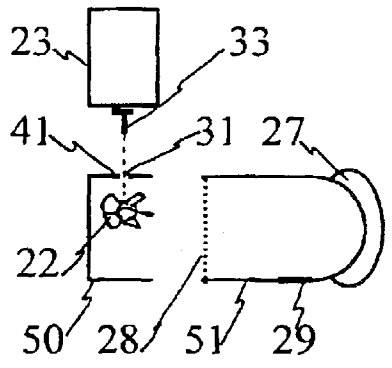

FIG. 7 shows the eyecup is detachable into two parts, where 51 is the front portion and 50 is the rear portion. This embodiment shown shaft 33 of the driver 23 is detached from the agitator 22, where the agitator 22 stays inside the rear portion of the eyecup 50. Seal 41 is shown mounted in the opening 31. When it is assembled, the shaft 33 of the driver 23 enters through seal 41 to avoid the eyewash liquid leakage around it. As in previous figures, 27 is a rim, 28 is a grill, and 29 is magnetic strip. It is shown assembled in FIG. 9.

Figure 8:
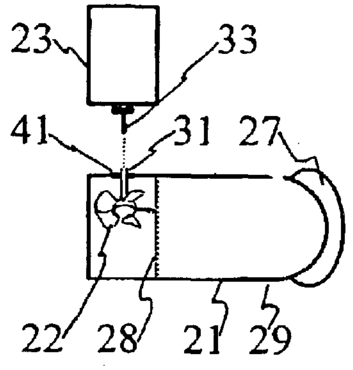

FIG. 8 similar to FIG. 7 except the eyecup 21 does not come apart and the agitator 22 has an extended hollow shaft, extending out through seal 41 where seal 41 is mounted in the opening 31 of eyecup 21. When it is assembled, shaft 33 of driver 23 enters the hollow shaft of the agitator 22. This embodiment of the apparatus is used to make internal parts of the apparatus corrosion resistive in which the agitator is made of corrosion resistive material and is shown assembled in FIG. 9.

Figure 9:
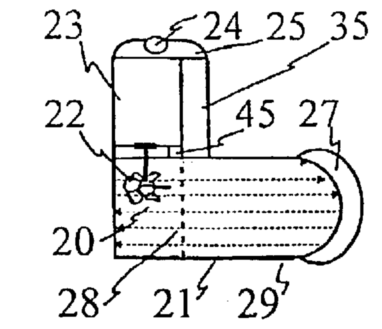
FIG. 9 is an assembled device of the embodiments shown in FIG. 7 and FIG. 8.

FIG. 9 is similar to FIG. 1 except in this figure, opening 45 is added. Opening 45 in the housing 25 is placed between the driver 23 and the eyecup 21 to drain eyewash liquid accumulation in case the seal 41 leaks. The seal 41 is shown in FIG. 7 and FIG. 8. FIG. 9 is an assembled embodiment of FIG. 7 and FIG. 8, where 20 is eyewash liquid in the eyecup 21. Agitator 22 is mounted on the shaft of driver 23. FIG. 9 shows momentary switch 24, housing 25, and access door 35, 27, 28, and 29 are the rim, grill, and magnetic strip respectively.

Figure 10:
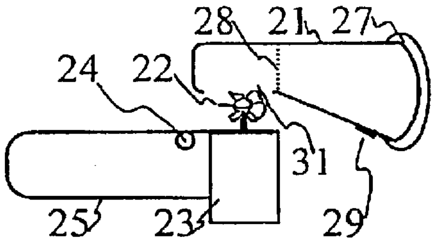
FIG. 10 shows another embodiment that is laid out differently and the outlook of the eyecup is different.

FIG. 10 is another embodiment of the apparatus were housing 25 for the driver 23, the power source and the momentary switch 24 for the driver 23 are laid out differently. The eyecup 21 is shaped differently and is detachable from the housing 25. 31 is an opening of the eyecup 21. Agitator 22 stays on the driver 23. Although it is not shown, the housing 25 may have a switching mechanism that will not to let the driver operate unless the eyecup 21 is attached to it. All other numbers correspond to the embodiment of FIG. 1.

Figure 11:
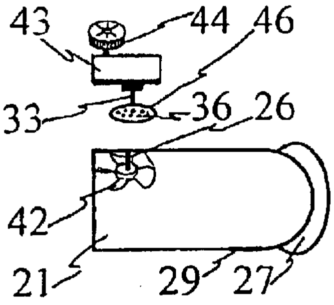
FIG. 11 shows a hand-operated driver and magnetic coupling between the agitator and the driver where the agitator is ferrous metal impregnated.

FIG. 11 has a hand-operated driver 43 instead of an electric motor as shown in the previous embodiments. Driver 43 is an arrangement of gears that achieve the proper speed where a thumb wheel 44 is used to operate the driver 43. Instead of a thumb wheel, a hand crank or a spring-loaded hand winding mechanism may be used. This embodiment may also use a magnetic coupling to transfer the power from the driver 43 to the agitator 42. Here, the disc 46 is impregnated with magnetic segments 38 and it is installed on the shaft 33 of the driver 43. Further, the disc 48 is aligned with agitator 42 to form the magnetic coupling that transfers the power from driver 43 to agitator 42. Agitator 42 may be made of ferrous metal or impregnated with ferrous metal and can be impregnated with magnetic segments to match the disc 46 as well. This embodiment has no opening in the wall of the eyecup 21 or a direct coupling between disc 48 and agitator 42 except magnetic force. Axle 26 of the agitator 42 is attached to the wall of the eyecup 21. FIG. 11 also shows the magnetic impregnation 36. When the device is assembled, the magnetic force creates a coupling between agitator 42 and disc 48 and driver 43 turns the disc 48 and agitator 42 inside the eyecup 21. As in previous figures FIG. 11 shows rim 27 and magnetic strip 29. The remaining assembly may be similar to FIG. 1.

Figure 12:
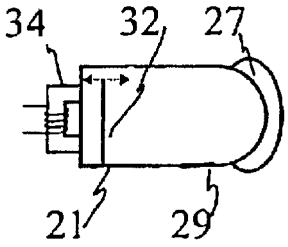
FIG. 12 shows an electromagnetic driver and a ferrous metal impregnated straight laid agitator mounted inside the eyecup.

FIG. 12 has an entirely different agitator and driver. Agitator 32 is a straight blade impregnated with ferrous metal mounted inside the eyecup 21 to stir the eyewash liquid. A driver 34, comprising an electromagnet with an oscillator to control its energizing frequency is placed outside of the eyecup 21. When driver 34 is energized, it pulls the agitator 32 towards it and when it is de-energized, the releases the agitator 32 to its original position, thereby causing the agitator 32 to move back and forth. This movement creates agitation in the eyecup 21 and to the eyewash liquid 20 inside of the eyecup 21. The oscillator is not shown in the diagram because it is well-known art. The rest of the powering, controlling and housing systems for this driver may be similar to the embodiment in FIG. 1.

Figure 13:
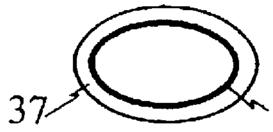
FIG. 13 shows a detachable adapter rim.
Figure 14:
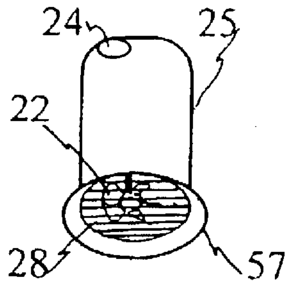
FIG. 14 shows an eyecup having a rim onto which a detachable adapter rim may attach.

FIG. 13 shows a detachable adapter rim 37 with a groove 47 to fit on the rim of a straight rim eyecup shown in FIG. 14. This detachable adapter rim 37 may be used on previously known eyecups or manufacturing conveniences.

FIG. 14 shows an eyecup having a straight rim 57, the groove 47 of the detachable adapter run 37 shown in FIG. 13 fits onto rim 57. The remaining numbers correspond to the embodiment in FIG. 1.

Figure 15:
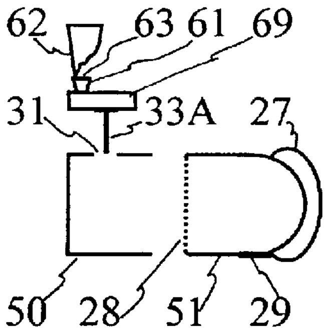
FIG. 15 shows an explicit view of the detachable eyecup to be used with an electrical toothbrush handle.
Figure 18:
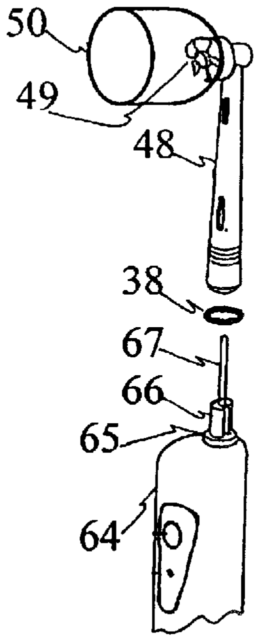
FIG. 18 shows one of the numerous electrical toothbrush handles available in the market and a detachable eyecup.

FIG. 15 shows an eyecup useable with an electrical toothbrush handle 64 (manufacturer Braun model number D8511) shown in FIG. 18. Where the electrical toothbrush handle moving parts don't move in circular motion to get proper agitation inside the eyecup a gearbox 69 is added. It has a skirt 62, inside of skirt 62 a sub skirt 61, a port 63 to engage the toothbrush handle 63 to power the gearbox and a shaft 33A for the agitator. Input port 63 fits on output shaft 67, sub skirt 61 fits on lug 66 to hold the eyecup in place and skirt 62 fits on ring 65 of the toothbrush handle 64 shown in FIG. 18. Remaining numbers correspond to the eyecup shown in FIG. 7.

Figure 16:
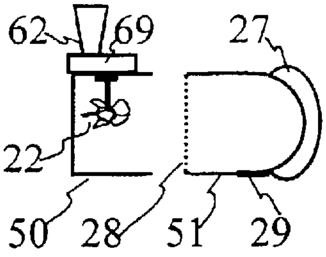
FIG. 16 shows assembled mechanism.

FIG. 16 shows the assembly of FIG. 15. All numbers correspond to FIG. 15 except components 31, 61 and 63 are not shown and agitator 22 added on the gear box shaft 33 A.

Figure 17:
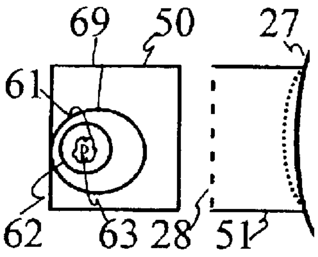
FIG. 17 shows top view of the device in FIG. 16.

FIG. 17 shows a top view of the eyecup of the FIG. 15 including rim 27, posterior eyecup component 50, front eyecup component 51, sub skirt 61, skirt 62, gearbox port 63 and gearbox 69.

FIG. 18 shows the electrical toothbrush handle 64, it's nonmoving parts 65, 66 and moving part 67. It's manufacturer is Braun having model number D8511, it also shows an eyecup built around the toothbrush head where bristles are replaced with an agitator. A seal or ring 38 provided by the manufacturer. The body of toothbrush 64 in this case may have an eyecup attachment stem 48, agitator 49 and posterior eyecup 50.

Although the present invention has been described with reference to preferred embodiments, numerous modifications and variations can be made and still the result will come within the scope of the invention. No limitation with respect to the specific embodiment disclosed herein is intended or should be inferred.

All figures illustrate eyecup 21.

Opening 31 an opening of the driver and agitator. Seal 41 used to avoid eyewash liquid leakage if the embodiments shown in FIG. 7 and FIG. 8 are applied.

Items 22, 32 and 42 are different types of agitators. 42 is an agitator impregnated with ferrous metal and 32 is a straight blade type agitator also impregnated with ferrous metal.

Items 23, 34 and 43 are three different types of drivers of the agitators where 23 is an electrical motor, 34 is an electromagnet mounted inside the eyecup and 43 is a thumb wheel operated driver. 33 is a shaft of the driver 23 and 43. 33A is a shaft of gearbox 69 for the agitator.

The momentary switch 24 that turns the driver has special circuitry to shut the driver off after a predetermined time. 44 is a thumb wheel that powers the driver.

Housing 25 holds the driver and its power and control source. 35 is an access door for the power source. Opening 45 in the housing drains liquid to avoid accumulation of eyewash liquid between the driver and the eyecup.

Magnetic segment impregnated disc 46 makes a magnetic coupling with axle 26 in which 36 is the magnetic impregnation.

Rim 27 is contoured to fit the eye orbital area. Detachable adapter rim 37 and groove 47 fit onto the straight rim 57 of the eyecup 21.

Grill 28 keeps the user away from the agitator 22.

Magnetic strip 29 attracts the ferrous metal particles during the eye washing procedure.

Dotted lines and arrows 20 show the eyewash liquid inside of the eye cup.

Area 49 illustrates where bristles are replaced with an agitator, stem 48 is a part of the eyecup which fits on the toothbrush, and 38 is a seal.

The toothbrush handle 64 is conventional in which items 65, 66 are nonmoving parts and 67 is a moving part of the toothbrush handle 64.

69 is an arrangement of gears to achieve proper agitation. The agitator shaft is designated by 33A, the sub skirt labelled 61, the skirt is labelled 62 and an input powering port for the gearbox 69 is designated by 63.

What is claimed is:

1. A handheld eye washer apparatus comprising:

an eyecup having a rim shaped to fit around at least one eye socket and a cup portion spanning the rim which is capable of holding a cleansing fluid; and a movable agitator supported for movement within the cup portion to agitate the fluid against an eye of said at least one eye socket.

2. The apparatus of claim 1 further comprising an electric motor and a power source mounted to the eyecup for driving movement of the agitator.

3. The apparatus of claim 2 further comprising a momentary switch for operating the electric motor.

4. The apparatus of claim 3 wherein there is provided a stop timer for automatically ceasing operation of the agitator upon expiration of an elapsed period of time.

5. The apparatus of claim 1 wherein the agitator further comprises a hand operated driver mechanism.

6. The apparatus of claim 5, wherein the hand operated driver mechanism further comprises a gear set and a hand operated power source.

7. The apparatus of claim 1 wherein the agitator further comprises an oscillating blade.

8. The apparatus of claim 1 further comprising a grill in the eyecup.

9. The apparatus of claim 1 further comprising a magnetic element affixed to the eyecup.

10. The apparatus of claim 1 further comprising a housing attached to the eyecup, said housing having a watertight wall adjacent to the eyecup between the agitator supported within the cup portion and a driver mechanism of the agitator supported within the housing.

11. The apparatus of claim 10, wherein the housing further comprises a removable panel.

12. The apparatus of claim 10, wherein the housing is mounted at a substantially right angle to the eyecup.

13. The apparatus of claim 10, wherein the housing is mounted distally from the rim.

14. The apparatus of claim 10, wherein the housing further comprises a body selectively separable from the eyecup.

15. The apparatus of claim 14 wherein the driver mechanism and the agitator are selectively separable from one another.

16. The apparatus of claim 14, further comprising a lock-out mechanism to prevent operation of the agitator when the housing is separated from the eyecup.

17. The apparatus of claim 10, wherein the eyecup further comprises an opening to receive a shaft there through coupled between the driver mechanism and the agitator.

18. The apparatus of claim 17, wherein the housing is selectively separable from the eyecup and the agitator is selectively separable from the shaft.

19. The apparatus of claim 17, wherein the opening is sealed about the shaft.

20. The apparatus of claim 10, wherein the housing further comprises a magnetic coupling to transfer power between the driver mechanism and the agitator.

21. The apparatus of claim 1, wherein the eyecup further comprises at least two separable members, and one of said members houses the agitator.

22. The apparatus of claim 21 further comprising a housing attached to the member housing a driver for the agitator, said housing having a watertight wall adjacent to the eyecup.

23. The apparatus of claim 22, wherein the housing further comprises an opening to ambient to drain cleansing fluid therefrom.

24. The apparatus of claim 1, wherein the rim further comprises an adapter rim removably attached to the rim.

25. The apparatus of claim 24, wherein the adapter rim further comprises a mounting mechanism for attaching to the rim.

26. The apparatus of claim 25, wherein the mounting mechanism further comprises a mounting groove for attaching to the rim.

27. The apparatus of claim 1, wherein the eyecup includes a longitudinal axis and wherein there is provided a housing having its longitudinal axis mounted parallel to the longitudinal axis of the eyecup.

28. The apparatus of claim 27, wherein the housing houses an electric motor, and a power source for driving movement of the agitator within the cup portion.

29. The apparatus of claim 1 wherein there is provided a housing mounted to the eyecup, distally from the rim and an electromagnet driver mechanism supported within the housing for driving movement of the agitator within the cup portion.

30. The apparatus of claim 29, wherein the impeller further comprises an oscillating rod.

31. The apparatus of claim 1, wherein the eyecup is molded in a single piece.

32. The apparatus of claim 1, wherein the agitator and the eyecup are selectively separable from one another, the eyecup being disposable for replacement thereof.

33. A handheld eye washer apparatus comprising:

an eyecup having a rim shaped to fit around at least one eye socket and a cup portion spanning the rim which is capable of holding a cleansing fluid;

a movable agitator supported for movement within the cup portion to agitate the fluid against an eye of said at least one eye socket; and a driver mechanism adapter supported on the eyecup and coupled to the agitator, the driver mechanism adapter being arranged for connection with a conventional electric toothbrush handle in place of a toothbrush attachment normally connected to the electric toothbrush handle for driving the agitator with a conventional electric toothbrush by communication through the driver mechanism adapter.

* * * * *